United States Patent [19]

Niimura et al.

[11] Patent Number: 5,508,298
[45] Date of Patent: Apr. 16, 1996

[54] AZOLE DERIVATIVE AND PHARMACEUTICAL COMPOSITION

[75] Inventors: Koichi Niimura, Saitama; Takao Ando; Toyohiko Nitta, both of Tokyo; Yuko Ikeda, Chiba, all of Japan

[73] Assignee: Kureha Chemical Industry Co., Ltd., Tokyo, Japan

[21] Appl. No.: 444,027

[22] Filed: May 18, 1995

Related U.S. Application Data

[62] Division of Ser. No. 137,045, Oct. 14, 1993.

[30] Foreign Application Priority Data

Feb. 12, 1992 [JP] Japan .................................. 4-61441

[51] Int. Cl.⁶ .......................... A61K 31/41; C07D 249/08
[52] U.S. Cl. .......................... 514/383; 548/267.8
[58] Field of Search .......................... 514/383; 548/267.8

[56] References Cited

U.S. PATENT DOCUMENTS 5,256,683 10/1993 Hutt et al. .

FOREIGN PATENT DOCUMENTS 0324646 7/1989 European Pat. Off. .
0413448 2/1991 European Pat. Off. .
3197464 8/1991 Japan .

*Primary Examiner*—Patricia L. Morris
*Attorney, Agent, or Firm*—Sughrue, Mion, Zinn, Macpeak & Seas

[57] ABSTRACT

A novel azole derivative of the general formula (I):

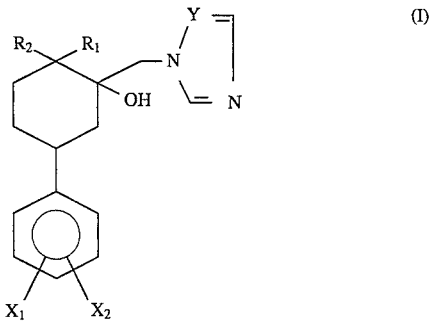

wherein $R_1$ and $R_2$ are, independently from each other, a hydrogen atom or an alkyl group having 1 to 4 carbon atoms, $x_1$ and $x_2$ are, independently from each other, a hydrogen or halogen atom, or hydroxyl, cyano, or trifluoromethyl group, and Y is CH or a nitrogen atom, a process for the production thereof, and a pharmaceutical composition containing the same as the active ingredient.

14 Claims, No Drawings

AZOLE DERIVATIVE AND PHARMACEUTICAL COMPOSITION

This is a Divisional of application Ser. No. 08/137,045 filed on Oct. 14, 1993, which was derived from International Patent Application No. PCT/JP93/00181 filed on Feb. 12, 1993.

TECHNICAL FIELD

The present invention relates to a novel azole derivative, a process for the production thereof, and a pharmaceutical composition containing the azole derivative as an active ingredient (more particularly, an antifungal agent or an aromarase inhibitor).

BACKGROUND ART

The recent development of pharmaceuticals and the advancement of medical techniques conquered many diseases. On the other hand, such treatment caused the depression in the immune systems. The depression became a major cause of the increase in patients susceptible to infection. These patients suffered at a high rate from deep-seated fungal diseases of opportunistic infections such as candidiasis, aspergillosis, and cryptococcosis. The measure to solve the problem became serious. Therefore, active research has been under way to develop drugs more superior than the conventional antifungal agents. For example, Japanese Unexamined Patent Publication (Kokai) No. 3-187464 discloses an azole derivative having a cyclohexanol ring and azole ring as basic structures. Such antifungal agents exhibit an antifungal activity by functioning on the cytochrome p450 in the fungus and inhibiting the production of ergosterol which is a constituent element of cell walls. Further, it is known that because the above antifungal agents function on the cytochrome p450, some of them exhibit an activity to inhibit aromarase [*J. Med. Chem.*, 33 (11), 2933–2942 (1990)].

From the results of the research on azole derivatives having applicability to broader fields and exhibiting a more superior antimicrobial activity, the inventors of the present invention found a novel azole derivative which has a low toxicity, and which exhibits activity against many fungi, and activity to inhibit an aromarase. The present invention is based on the above findings.

DISCLOSURE OF THE INVENTION

Therefore, the present invention relates to a compound of the general formula (I):

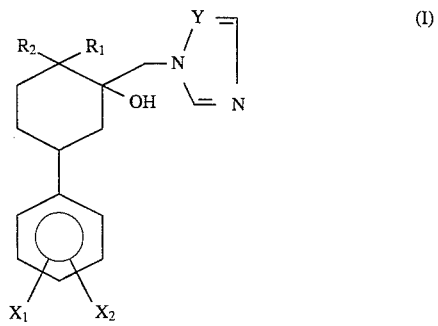

wherein $R_1$ and $R_2$ are, independently from each other, a hydrogen atom or an alkyl group having 1 to 4 carbon atoms, $X_1$ and $X_2$ are, independently from each other, a hydrogen or halogen atom, or hydroxyl, cyano or trifluoromethyl group, and Y is CH or a nitrogen atom, or a salt thereof. In the above general formula (I), preferably, $R_1$ and $R_2$ are, independently from each other, a hydrogen atom or an alkyl group having 1 to 2 carbon atoms, $X_1$ and $X_2$ are, independently from each other, a hydrogen or halogen atom, or hydroxyl group, and Y is CH or a nitrogen atom.

Further, the present invention relates to a compound of the general formula (III):

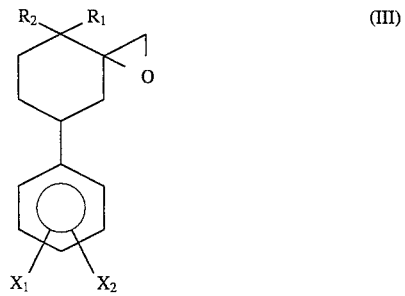

wherein $R_1$, $R_2$, $X_1$, and $X_2$ have the same meanings as above, or a salt thereof.

Further, the present invention relates to a compound of the general formula (IV):

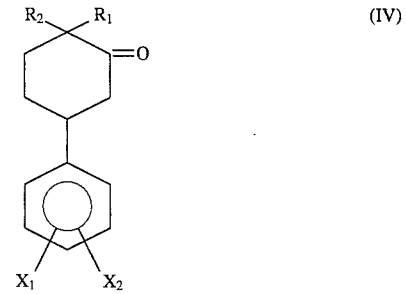

wherein $R_1$, $R_2$, $X_1$, and $X_2$ have the same meanings as above, or a salt thereof.

Still further, the present invention relates to a process for the production of a compound of the general formula (I) characterized by reducing a compound of the general formula (V):

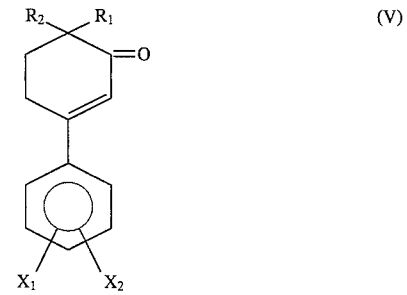

wherein $R_1$, $R_2$, $X_1$, and $X_2$ have the same meanings as above, to obtain the compound of the general formula (IV), reacting the resulting compound of the general formula (IV) and an S-ylide compound to obtain the compound of the general formula (III), and reacting the resulting compound of the general formula (III) and a compound of the general formula (II):

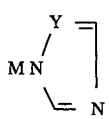

(II)

wherein M is a metal ion and Y has the same meaning as above.

Still further, the present invention relates to a pharmaceutical composition, particularly, an antifungal agent or an aromatase inhibitor, characterized by containing a compound of the general formula (I) or a salt thereof.

BEST MODE FOR CARRYING OUT THE INVENTION

In the general formulae (I), (III), (IV), or (V), the alkyl group of 1 to 4 carbon atoms as the group $R_1$ or $R_2$ is a methyl, ethyl, straight-chain or branched propyl, or straight-chain or branched butyl group. The halogen atom is a chlorine, bromine, iodine, or fluorine atom. Further, in the general formula (II), the metal ion M is an alkali metal, for example, sodium or potassium.

The azole derivative of the general formula (I) [hereinafter sometimes referred to as the present compound (I) or the present azole compound (I)] may be manufactured, for example, from a compound of the general formula (V) by a process comprising the following steps (a), (b), and (c).

(a) The compound of the general formula (V) is reduced to obtain the compound of the general formula (IV) [hereinafter sometimes referred to as the present cyclohexanone compound (IV)].

(b) The resulting present cyclohexanone compound (IV) is reacted with an S-ylide compound to obtain the compound of the general formula (III) [hereinafter sometimes referred to as the present oxolane compound (III)].

(c) The present oxolane compound (III) is reacted with the 1,2,4-triazole or imidazole of the general formula (II), thereby obtaining the present azole compound (I).

As the diluents which may be used in the series of reactions in the steps (a), (b), and (c), there may be mentioned hydrocarbons, such as benzene, toluene, xylene or hexane; halogenated hydrocarbons, such as methylene chloride, chloroform or carbon tetrachloride; alcohols, such as methanol, ethanol or isopropyl alcohol; ethers, such as diethyl ether, diisopropyl ether, tetrahydrofuran or dioxane; and further, ethyl acetate, acetonitrile, acetone, dimethylformamide, or dimethyl sulfoxide.

Further, the series of reactions in steps (a), (b), and (c) may also be carried out in the presence of a base or acid, in addition to the above diluent. As the bases which can be used, there may be mentioned carbonates of alkali metals, such as sodium or potassium carbonate; hydroxides of alkali metals, such as sodium or potassium hydroxide; alcoholates of alkali metals, such as sodium methylate, sodium ethylate or potassium t-butylate; hydride of alkali metals, such as sodium or potassium hydride; alkylates of alkali metals, such as n-butyl lithium; and further, triethylamine, or pyridine. Further, as the acids, there may be mentioned inorganic acids, such as hydrochloric, hydrobromic, hydriodic, or sulfuric acid; organic acids, such as formic, acetic, butyric, or p-toluenesulfonic acid.

The reducing reaction in the step (a) may be carried out in the presence of, for example, a platinum catalyst, palladium carbon and potassium carbonate or palladium carbon, and a conventional oxidizing agent, such as Jone's reagent.

That is, the compound of the general formula (V) is dissolved in an organic solvent (for example, alcohol), a palladium carbon catalyst is added, and the reducing reaction is carried out for about 5 to 24 hours in a hydrogen stream. Then, the solvent is removed, an organic solvent is further added, Jone's reagent or the like is added, and the oxidation reaction is carried out. After the reaction is ceased by adding alcohol (for example, isopropyl alcohol), the resulting product is poured into ice water, extracted with a solvent (for example, ethyl acetate, diethyl ether). The product is dried over sodium sulfate or the like to remove the solvent, and the residue is purified by column chromatography to obtain the desired present cyclohexanone compound (IV). In the cyclohexene ring of the compound of the general formula (V used as the starting material and the cyclohexane ring of the present cyclohexanone compound (IV), the configurations at the ring carbon atom to which the groups $R_1$ and $R_2$ are bonded and the chiral ring carbon atom to which the phenyl group is bonded are not limited. Each of the optical isomers having any configuration or a mixture thereof may be used. The optical isomers may be resolved and purified by chromatography (for example, thin layer chromatography, column high performance liquid Chromatography, or optical isomer separation column chromatography) and a general method of optical isomer separation. The compound of the general formula (V) may be prepared by the method described in, for example, *Monalsh Chem.* 9, 1043, 1960.

The present cyclohexanone compound (IV) includes the optical isomers of the following general formulae (IVA), (IVA'), (IVB), and (IVB'):

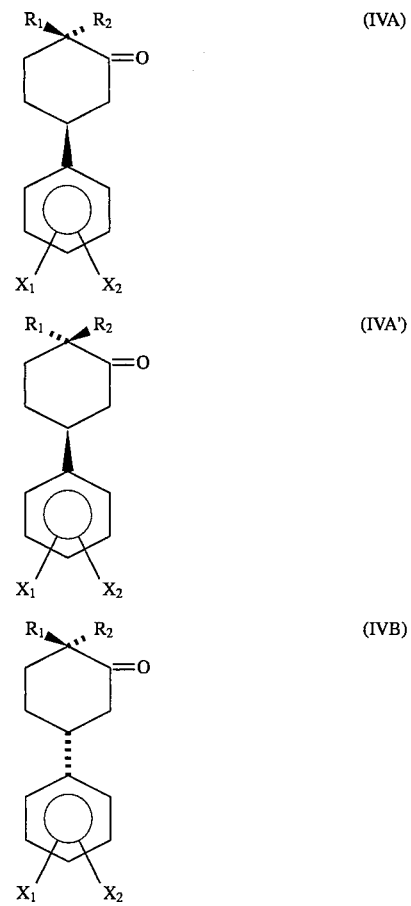

-continued

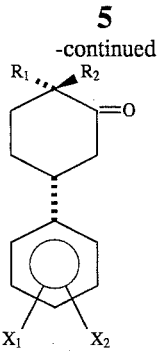
(IVB')

wherein $R_1$, $R_2$, $X_1$, and $X_2$ have the same meanings as above.

The purification is performed by recrystallization, silica gel column chromatography, or the like. In the step (b), the configurations at the asymmetric carbon atoms in the rings of the starting compound and the final compound are not limited. Each of the pure optical isomers having any configuration or mixtures thereof may be used. The optical isomers may be resolved and purified in the same manner as above. The present oxolane compound (III) includes optical isomers of the following general formulae [III(t-(+))], [III(t-(−))], [III(c-(−))], and [III(c-(+))]:

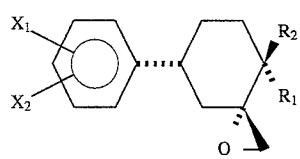
[III(t-(+))]

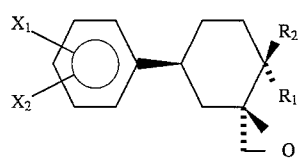
[III(t-(−))]

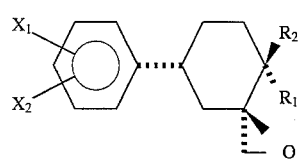
[III(c-(−))]

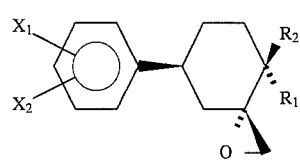
[III(c-(+))]

wherein $R_1$, $R_2$, $X_1$, and $X_2$ have the same meanings as above.

The reaction of the step (c) may be performed by dissolving the 1,2,4-triazole or imidazole of the general formula (II) in the above-mentioned diluent, and adding the present oxolane compound (III), in the presence of the above-mentioned base as occasion demands, or alternatively, by dissolving the present oxolane compound (III) in the diluent, and then adding the 1,2,4-triazole or imidazole of the general formula (II). The reaction temperature is about 0° to 150° C., preferably about 40° to 120° C., and the reaction time is about 0.5 to 24 hours, preferably about 1 to 10 hours. After the above-mentioned reaction is completed, the reaction mixture is cooled and extracted in ice water with an organic solvent, such as ethyl acetate, chloroform, methylene chloride, diethyl ether, or benzene to separate the organic layer. Then, the organic layer is washed with water and dried. Further, the solvent is removed under reduced pressure and the resulting residue is purified to obtain the desired present azole compound (I). The purification is performed by recrystallization, silica gel column chromatography, or the like. In the step (c), the configurations at the chiral carbon atoms of the starting compound and the final compound are not limited. Each of the pure optical isomers having any configuration or mixtures thereof may be used. The present azole compound (I) includes the optical isomers of the following general formulae [I(t-(+))], [I(t-(−))], [I(c-(−))], and [I(c-(+))]:

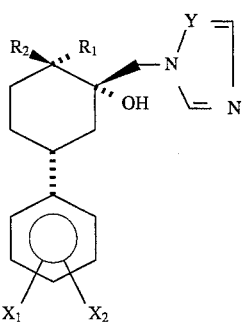
[I(t-(+))]

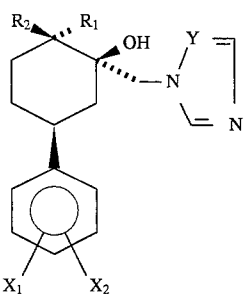
[I(t-(−))]

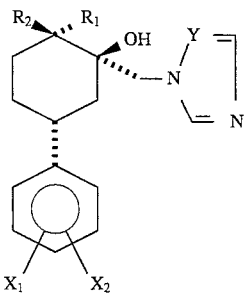
[I(c-(−))]

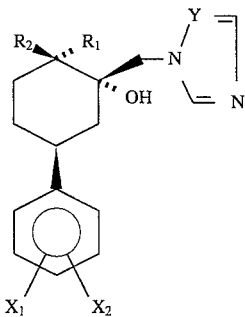
[I(c-(+))]

wherein $R_1$, $R_2$, $X_1$, and $X_2$ have the same meanings as above.

The present azole compound (i) exhibits a pharmacological activity, in particular an antifungal activity, and is useful for overcoming fungal infections in mammals, including humans. Therefore, the present invention relates also to a pharmaceutical composition, particularly, antifungal agent, containing the present azole compound (I) or a pharmaceutically or veterinarily acceptable salt thereof, and a pharmaceutically or veterinarily acceptable diluent or carrier. The antifungal agent of the present invention is useful for the treatment of local fungal infections in humans, particularly those caused by fungi belonging to the genera Candida, Trichophyton, Microsporum, or Epidermophyton, or infections of the mucous membranes caused by Candida albicans (for example, oral Candidiasis or vaginal Candidiasis). Further, the antifungal agent of the present invention may also be used for the treatment of systemic fungal infections caused by *Candida albicans, Cryptococcus neoformans, Aspergillus fumigatus*, or fungi belonging to the genera Coccidioides, Paracoccidioides, Histoplasma, or Blastomyces.

The antifungal activity of the present azole compound (I) in a living body was evaluated by determining the minimum inhibitory concentration (MIC) in vitro for the fungi belonging to the genera Candida, Cryptococcus, Aspergillus, and Trichophyton.

The present azole compound also exhibits an aromatase inhibitory activity, and an antitumor activity along with the aromarase inhibitory activity. Therefore, the present invention also relates to an aromatase inhibitory agent, particularly an antitumor agent, containing the present azole compound (I) or a pharmaceutically or veterinarily acceptable salt thereof, and a pharmaceutically or veterinarily acceptable diluent or carrier. Aromarase is an enzyme which aromatizes the ring A of many steroid hormones in the course of metabolism. Further, many cancers (for example, breast cancer, cancer of the uterus, prostate cancer, pancreatic cancer, ovarian cancer, or the like) depend on the steroid hormone having the aromatic ring A. Therefor, the present azole compound (I) exhibits an antitumor activity on these cancers.

The aromarase inhibitory activity was determined by the method of Covey, D. F. et al., [BBRC (1), 81–86, 1988]. That is, the aromarase inhibitory activity was determined as the 50% inhibitory concentration $IC_{50}$ value of the enzyme activity of the compound to be tested, whereupon the $IC_{50}$ value of the present azole compound (I) was not more than $10^{-6}$M.

The present azole compound (I) may be mixed with a carrier generally acceptable for pharmaceutical compositions, and used in the form of various formulations. These compositions may be formulated into units of dosage containing about 1 to 600 mg, more preferably about 5 to 500 mg, of the present azole compound (I) in the form of dosage. The present azole compound (I) may be a salt, such as a sulfate, nitrate, or citrate. The pharmaceutical composition of the present invention may be administered orally, endermically, or intravenously.

When treating adults, it is suitable to administer about 0.1 to 100 mg/kg in one dosage or divide into several dosages. However, the actual dosage is determined by the physician with reference to the age of the individual patient, the seriousness of the symptoms, and the route of administration, so the range of the dosage mentioned above may be sometimes exceeded, but these cases are also included in the scope of the present invention. The acute toxicity ($LD_{50}$) of the present azole compound (I) was found using ICR mice to be over 500 mg/kg, so it is apparent that the present azole compound (I) is safe.

EXAMPLES

The present invention now will be further illustrated by, but is by no means limited to, the following examples. In the following examples, the NMR was measured using a JNM-GSX500 (Nihon Denshi), the infrared absorption spectra were measured using a Nihon Bunko A-202 apparatus, and the optical rotation was measured using a Nihon Bunko automatic polarimeter DIP-360.

Example 1

[1] Preparation of (2,2-dimethyl)-5-(4-fluorophenyl)-5-cyclohexene-1-one [V-1].

1-bromo-4-fluorobenzene (7.06 g, 40 mmole) was dissolved in 20 ml of tetrahydrofuran, then the resulting solution was stirred at −78° C. in an argon gas stream. N-butyl lithium (25.2 ml, 1.6 mole solution) was added slowly and the solution was allowed to stand for 15 minutes. A solution of 5 g (40 mmole) of 4,4-dimethyl-2-cyclohexene-1-one in 20 ml of tetrahydrofuran was slowly added to the above solution, and then, the resulting solution was allowed to stand for 30 minutes. Thereafter, a saturated aqueous solution of ammonium chloride was added, the whole solution was poured into ice water, and extracted with ethyl acetate. The organic layer was dried over sodium sulfate to remove the solvent. 20 ml of acetone was added to the residue, until the Jone's reagent previously prepared no longer changed color (until it no longer became green). After 30 minutes, the reaction was ceased by adding isopropyl alcohol. The whole was poured into ice water, and the crude product was extracted with ethyl acetate. The organic layer was dried over sodium sulfate to the solvent was removed by evaporation. The residue was purified by column chromatography (10% ethyl acetate/hexane) to obtain the above-titled compound [V-1] (7.8 g).

$^1$H-NMR ($\delta$ ppm; $CDCl_3$) 1.17 (s, 6H), 1.97 (t, 2H, J=11.9 Hz), 2.75 (t, 2H, J=11.9 Hz), 6.30 (s, 1H), 7.10, 7.55 (each m, 2H)

[2] Preparation (2,2-dimethyl)-5-(4-fluorophenyl)-cyclohexane-1-one [IV-1]

The compound [V-1] (4 g, 18.3 mole) obtained in the Example 1[1] was dissolved in 20 ml of ethyl alcohol. After 100 mg of 10% palladium carbon was added, the solution was stirred overnight in a hydrogen gas stream. The next morning, the reaction solution was filtered, and the solvent was evaporated. Then, 10 ml of acetone was added to the residue, and Jone's reagent previously prepared was added until the reagent no longer changed in color (until no longer becoming green). After 30 minutes, the reaction was ceased by adding isopropyl alcohol. The solution was poured into ice water and extracted with ethyl acetate. The organic layer was dried over sodium sulfate, and the solvent was evaporated. The residue was purified by column chromatography (10% ethyl acetate/hexane) to obtain the above-titled compound [IV-1] (3.27 g).

$^1$H-NMR ($\delta$ ppm; $CDCl_3$)

1.12, 1.24 (each s, 3H), 1.65 to 2.05 (m, 4H), 2.47, 2.71 (each m, 1H), 2.96 (m, 1H), 7.02, 7.18 (each m, 2H) IR (vmax; KBr): 1690, 1602

Example 2

[1] Preparation of t-(+)-(2,2-dimethyl)-5-(4-fluorophenyl)-cyclohexane-1,1'-oxolane [III(t-(+))-1] and t-(−)-(2,2-dimethyl)-5-(4-fluorophenyl)-cyclohexane-1,1'-oxolane [III(t-(−))-2]

To a mixture of 5 ml of dimethyl sulfoxide and 10 ml of tetrahydrofuran, 499.2 mg (20.8 mmole) of sodium hydride which had been washed with n-hexane was suspended. 4.425 g (20.8 mmole) of trimethylsulfonium iodide was added to the suspension under cooling with ice. The mixture was stirred for 30 minutes, then 5 ml of a dimethyl sulfoxide solution of 4.2729 g (19.4 mmole) of the compound [v-1] obtained in the Example 1[1] was added dropwise slowly, whereupon the reaction solution turned light yellow. The solution was stirred overnight at room temperature. Then, the reaction was ceased by pouring the solution into 100 ml of ice water. The crude product was extracted with diethyl ether (100 ml×2 and 50 ml×1). The collected ether layers were washed with a saturated saline solution and dried over anhydrous sodium sulfate, then concentrated under reduced pressure to obtain an oily crude product (4.312 g). The crude product was purified by silica gel chromatography, whereupon the above-titled compounds [III(t(-(+))-1] and [III(t-(−))-2] (0.8726 g) were obtained as a racemic mixture mainly in the second peak with n-hexane:ethyl acetate (80:1).

$^1$H-NMR (δ ppm; CDCl$_3$) 0.80 (s, 3H), 1.15 (s, 3H), 1.23 (m, 1H), 1.5–1.8 (m, 4H), 2.29 (t, 1H), 2.49 (d, 1H, J=4.59 Hz), 2.92 (d, 1H, J=4.59 Hz), 2.72 (m, 1H), 6.98 (m, 2H), 7.16 (m, 2H)

[2] Preparation of (2,2-dimethyl)-5S-(4-fluorophenyl)-1R-(1H-1,2,4-triazole-1-ylmethyl)-cyclohexane-1-ol [I(t-(+))-1]

The racemic mixture (872.6 mg, 3.72 mmole) obtained in the Example 2[1] was dissolved in 10 ml of dimethyl formamide. A sodium salt of 1,2,4-triazole was added to the solution. The whole was heated and stirred in an argon atmosphere for 24 hours at 80° C. After the reaction was completed, the reaction solution was poured into ice water (50 ml) and the obtained crude product was extracted with diethyl ether (100 ml×2 and 50 ml×1). The collected ether layers were washed with 20 ml of a saturated saline solution and dried over anhydrous sodium sulfate, then concentrated under reduced pressure, whereupon a crude product (1.113 g) was obtained. The crude product was purified by silica gel chromatography (n-hexane:ethyl acetate=1:1) to obtain the desired product as a racemic mixture (0.7249 g). The racemic mixture was resolved by chiracell OG, whereupon the above-titled compound [I(t-(+))-1] (30.2 mg) was obtained in the second peak upon separation at 3 ml/min using 5% isopropyl alcohol/n-hexane solution as a moving phase at 40° C.

Melting point=155° to 156° C. Optical rotation (c=0.1; methanol)=+40°; Chemical purity=92%

Example 3

[1] Preparation of (2,2-dimethyl)-5R-(4-fluorophenyl)-1S-(1H-1,2,4-triazole-1-ylmethyl)cyclohexane-1-ol [I-(t-(−))-2]

The racemic mixture obtained in the Example 2[2] was separated under the conditions shown in the Example 3[2] using chiracell OG, whereupon the above-titled compound [I(t-(−))-2] (26.1 mg) was obtained in the first peak.

Melting point=156° to 157° C. Optical rotation (c=0.1; methanol)=−40°; Chemical purity=91.1%

Example 4

[1] Preparation of c-(−)-(2,2-dimethyl) 5-(4-fluorophenyl)-cyclohexane-1,1'-oxolane [III(c-(−))-3] and c-(+)-(2,2-dimethyl)-5 -(4-fluorophenyl)-cyclohexane-1,1-oxolane [III(c-(+))-4]

Trimethylsulfoxoniumiodide (5.831 g, 26.5 mmole) was placed in a 100 ml eggplant type flask and dissolved in 30 ml of dimethyl sulfoxide. 629.1 mg (26.2 mmole) of sodium hydride which had been washed with n-hexane was added to the above solution. The solution was stirred at room temperature for 1 hour, whereupon the reaction solution became transparent. A solution of the above compound [IV-1] (3.85 g, 17.5 mmole) dissolved in 10 ml of dimethyl sulfoxide was added to the reaction solution. The whole was stirred at 10° C. for 5 minutes and at room temperature for 5 hours, whereupon the starting material disappeared. The resulting solution was dried over anhydrous sodium sulfate, and concentrated under reduced pressure by a rotary evaporator to obtain the crude product. The crude product was purified by silica gel chromatography, whereupon the above-titled compounds [III(C-(−))-3] and [III(C-(+))-4] were obtained as a racemic mixture in the first fraction of the n-hexane ethyl acetate (20:1).

$^1$H-NMR (δ ppm; CDCl$_3$) 0.79 (s, 3H), 1.16 (s, 3H), 1.23 (d, d, 1H), 1.51–1.58 (m, 4H), 2.28 (t, 1H), 2.42 (d, 1H, J=4.59 Hz), 2.84 (d, 1H, J=4.59 Hz), 2.90 (m, 1H), 6.97 (m, 2H), 7.1 (m, 2H)

[2] Preparation of (2,2-dimethyl)-5S-(4-fluorophenyl)-1S-(1H-1,2,4-triazole-1-ylmethyl)cyclohexane-1-ol [I(C-(−))-3]

The racemic mixture (4.00 g, 17.5 mmole) obtained from the Example 4[1] was dissolved in 35 ml of dimethylformamide. 12.65 g (26.5 mmole) of sodium salt of 1,2,4-triazole was added to the solution, and the whole was heated at 90° C. under stirring in an argon atmosphere for 4 hours. After the reaction was completed, the reaction solution was poured into 35 ml of ice water and the crude product was extracted with diethyl ether (150 ml×1, 50 ml×1, and 30 ml×1). The collected ether layers were washed with distilled water (20 ml×1) and dried over anhydrous sodium sulfate, then were concentrated under reduced pressure to obtain the desired racemic crude product. The racemic mixture was dissolved in ethyl acetate and the mother solution was purified by silica gel chromatography with ethyl acetate, whereupon the purified product of the racemic mixture was obtained. The racemic mixture was separated using chiracell OD ( separation conditions, moving phase; isopropyl ether: n-hexane=15:85, 1.2 ml/min) to obtain the above-titled compound [I(c-(−))-3] in the second peak.

Melting point=139° to 140° C. Optical rotation (c=0.01; methyl alcohol)=−41.7° Chemical purity=99.6%, Optical purity=99.4%

Example 5

[1] Preparation of (2,2-dimethyl)-5R-(4-fluorophenyl)-1 R-(1H-1,2,4-triazole-1-ylmethyl)cyclohexane-1-ol [I-(C-(+)-4]

A racemic mixture was obtained by the method described in the Example 4[2]. The resulting racemic mixture was separated using the above-mentioned chiracell OD used in the Example 4[2] under the same conditions to obtain the desired above-titled compound [I(c(+))-4] in the first peak.

Melting point=138° to 139° C. Optical rotation (c=0.01; methyl alcohol)=+43.0° Chemical purity=98.7%; Optical purity=100%

Example 6

[1] Preparation of (2,2-dimethyl)-5-(4-chlorophenyl)-5-cyclohexene-1-one [V-2]

1-bromo-4-chlorobenzene (7.66 g, 40 mmole) and 25 ml of dried tetrahydrofuran were placed in a 100 ml eggplant type flask. The whole was stirred in an argon atmosphere at room temperature and cooled to −78° C. Then, 25 ml (40 mmole) of n-butyl lithium was slowly added and the whole was stirred for 30 minutes. Then, 4.96 g (40 mmole) of 4,4-dimethyl-2-cyclohexene-1-one dissolved in dried tetrahydrofuran was added dropwise. After 90 minutes, 10 ml of a saturated aqueous solution of ammonium chloride was added, and the whole was poured into 10 ml of ice water. Thereafter, extraction was performed with diethyl ether (100 ml×2 and 50 ml×1). The ether layers were washed with a saturated saline solution and dried over anhydrous sodium sulfate, then was dried under reduced pressure. The crude product was purified by silica gel chromatography (n-hexane: ethyl acetate=4:1). The resulting yellow oily product (19.48 g; 82.29 mmole) was added to a 200 ml eggplant type flask, and 85 ml of acetone was added. After stirring, 25 ml of Jone's reagent was added dropwise. After 15 minutes, the reaction was ceased by adding 85 ml of cold water. Thereafter, the crude product was extracted with diethyl ether (100 ml×2), the ether layers were washed with a saturated saline solution, and dried over anhydrous sodium sulfate, and dried under reduced pressure. The residue was purified by silica gel chromatography (n-hexane:ethyl acetate=8:1) to obtain the above-titled compound [V-2].

$^1$H-NMR (δ ppm; CDCl$_3$) 1.17 (s, 3H), 1.97 (m, 2H), 2.75 (m, 2H), 6.32 (s, 1H), 7.38 (d, 2H, J=8.70 Hz), 7.48 (d, 2H, J=8.70 Hz) IR (vmax (cm$^{-1}$), KBr):1655, 1615, 1595

[2] Preparation of
(2,2-dimethyl)-5-(4-chlorophenyl)-cyclohexane-1-one
[IV-2]

10% palladium carbon was added to 5.06 g (21.6 mmole) of the compound [V-2] obtained in the Example 6[1], and ethanol was gently added thereto in an ice bath. Then, hydrogen gas was introduced at room temperature. The mixture was stirred overnight, the reaction solution was then filtered, and the filtrate was dried under reduced pressure. The residue was purified using silica gel chromatography to obtain a yellow oily product (4.72 g). The oily product (3.94 g) was placed in a 100 ml eggplant type flask, and 17 ml of acetone was added. Then, the whole was stirred. 3 ml of Jone's reagent was added thereto in an ice bath. After 90 minutes, the reaction was ceased by adding 20 ml of ice water. Extraction was performed with diethyl ether (50 ml×2). The ether layers were washed with a saturated saline solution, dried over anhydrous sodium sulfate and dried under reduced pressure. The residue was purified by silica gel chromatography (n-hexane:ethyl acetate=10:1) to obtain the above-titled compound [IV-2] (2.40 g).

Further, the above-titled compound [IV-2] or the compound [IV-1] were able to be produced by the following process:

6.32 g (33 mmole) of 1-bromo-4-chlorobenzene was dissolved in 30 ml of dried tetrahydrofuran and the solution was stirred in an argon atmosphere at −78° C. 20.6 ml (33 mmole) of an n-hexane solution of n-butyl lithium was slowly added to the solution. After stirred for 10 minutes, 1.34 mg (15 mmole) of copper cyanide was added. The whole was stirred at −78° C. for 40 minutes, whereupon the copper cyanide was substantially dissolved. Further, 5 ml of tetrahydrofuran was added, whereupon the reaction solution turned transparent. 1.86 g (15 mmole) of 2,2-dimethyl-5-cyclohexene-1-one was slowly added dropwise to the solution at −78° C. in an argon atmosphere. The reaction solution changed in color from a light orange to a light yellow and the starting material disappeared. After stirring at −78° C. for 30 minutes, a saturated aqueous solution of ammonium chloride was added. The temperature of the reaction solution was raised from −78° C. to 0° C., and the crude product was extracted with diethyl ether (100 ml×1 and 50 ml×1). The ether layers were washed with a saturated saline solution (20 ml×1), dried over anhydrous sodium sulfate. The solvent was evaporated under reduced pressure to obtain the crude product (2.63 g). The crude product was purified using silica gel chromatography to obtain the above-titled compound [IV-2] (2.3 g) by n-hexane: ethyl acetate (10:1). When 1-bromo-4-fluorobenzene was used instead of 1-bromo-4-chlorobenzene, the compound [IV-1] was obtained. The physicochemical data of the above-titled compound [IV-2] is as follows: $^1$H-NMR (67ppm; CDCl$_3$) 1.21 (s, 3H), 1.24 (s, 3H), 1.69 (m, 1H), 1.85 (m, 1H), 1.91 (m, 1H), 1.99 (m, 1H), 2.47 (m, 1H), 2.71 (dd, 1H, J=1.37, 12.83 Hz), 2.95 (m, 1H), 7.15 (d, 2H, J=8.25 Hz) IR (vmax, cm$^{-1}$, KBr): 1710, 1510, 1150

[3] Preparation of
(t-(+))-(2,2-dimethyl)-5-(4-chlorophenyl)-cyclohexane- 1,1'-oxolane [III(t-(+))-5] and
(t-(−))-(2,2-dimethyl)-5-(4-chlorophenyl)-cyclohexane-1,1'-oxolane [III(t-(−))-6]

Dimethyl sulfoxide (2 ml) and 3 ml of dried tetrahydrofuran were added to 166.8 mg of sodium hydride (6.95 mmole) which had been washed with n-hexane, and the mixture was stirred at room temperature. A solution of trimethylsulfonium iodide (1.42 g, 6.95 mmole) dissolved in 4 ml of dimethyl sulfoxide was added in an ice bath. Further, a solution of 1.097 g (4.63 mmole) of the compound [IV-2] obtained in the Example 6[2] dissolved in 2 ml of dimethyl sulfoxide was added dropwise. The whole was washed with 2 ml of dimethyl sulfoxide. The mixture was stirred overnight, and the reaction was ceased with ice water. Extraction was performed with diethyl ether (50 ml×3). The ether layers were washed with a saturated saline solution, and dried over dried magnesium sulfate, and further dried under reduced pressure. The residue was purified by silica gel chromatography (n-hexane:ethyl acetate=20:1) to obtain the above-titled compounds [III(t-(+))-5] and [III(t-(−))-6] as a racemic mixture.

[4] Preparation of
(2,2-dimethyl)-5S-(4-chlorophenyl)-1R-(1H-2,4-triazole-1-ylmethyl)cyclohexane-1-ol [I(t-(+))-5]

A sodium salt of 1,2,4-triazole (301.1 mg, 3.3 mmole) was added to 552.9 mg (2.2 mmole) of the racemic mixture obtained in the Example 6[3]. 6 ml of dimethyl sulfoxide was added thereto, and the mixture was stirred in an oil bath at 80° C. in an argon atmosphere. After 5 hours, 20 ml of distilled water was added to cease the reaction. The crude product was extracted with diethyl ether (50 ml×4). The obtained ether layers were washed with a saturated saline solution, dried over anhydrous sodium sulfate, and further dried under reduced pressure. The residue was purified with silica gel chromatography (ethyl acetate) to obtain a racemic mixture. The resulting racemic mixture was separated by chiracell OD (moving phase=n-hexane containing 2% isopropyl alcohol; 1 ml/min) to obtain the above-titled compound [I(t-(+))-5] (25.4 mg) in the second peak.

Melting point=173° to 175° C. Optical rotation (c=0.5; methyl alcohol)=+65° C. Chemical purity: 98.0%

Example 7

[1] Preparation of (2,2-dimethyl)-5R-(4-chlorophenyl)-1S-(1H-1,2,4-triazole-1-ylmethyl)cyclohexane-1-ol [I(t-(−))-6]

The racemic mixture obtained in the Example 6 [4] was separated using chiracell OD (moving phase=n-hexane containing 2% isopropyl alcohol) to obtain the above-titled compound [I(t-(−))-6] (31.4 mg) in the first peak.

Melting point=176° to 177° C. Optical rotation (c=0.5; methyl alcohol)=−64° Chemical purity=99.9%

Example 8

[1] Preparation of (c-(−))-(2,2-dimethyl)-5-(4-chlorophenyl)-cyclohexane-1,1'-oxolane [III(c-(−))-7] and (c-(+))-(2,2-dimethyl)-5-(4-chlorophenyl)-cyclohexane-1,1'-oxolane [III(c-(+))-8]

3 ml of dimethyl sulfoxide was added to 72 mg (3 mmole) of sodium hydride which had been washed with n-hexane, and the mixture was stirred at room temperature. 660.2 mg (3 mmole) of trimethylsulfoxonium iodide was added to the mixture, and then, 5 mg (2.0 mmole) of the compound [IV-2] obtained in the Example 6[2] dissolved in 2 ml of dimethyl sulfoxide was added dropwise. The mixture was washed with 1 ml of dimethyl sulfoxide. The mixture was stirred overnight, and the reaction was ceased with 10 ml of cold water. The crude product was extracted with dimethyl ether (50 ml×3), and the extracts were dried under reduced pressure. The resulting residue was purified by silica gel chromatography (n-hexane:ethyl acetate=20:1) to obtain the above-titled compounds [III(c-(+))-7] and [III(c-(+))-8] as a racemic mixture.

[2] Preparation of (2,2-dimethyl)-5S-(4-chlorophenyl)-1S-(1H-1,2,4-triazole-1-ylmethyl)cyclohexane-1-ol [I(c-(−))-7]

A sodium salt of 1,2,4-triazole (301.1 mg, 3.3 mmole) was added to 552.9 mg (2.2 mmole) of the racemic mixture obtained in the Example 8[1], and dimethyl sulfoxide (6 ml) was further added. Then, the mixture was stirred in an oil bath at 80° C. in an argon atmosphere. After 5 hours, 20 ml of distilled water was added to cease the reaction. The crude product was extracted with diethyl ether (50 ml×4). The obtained ether layers were washed with a saturated saline solution, dried over anhydrous sodium sulfate, and further dried under reduced pressure. The residue was treated with silica gel chromatography (100% ethyl acetate) to obtain a purified racemic mixture. The resulting racemic mixture was purified by chiracell OD (moving phase; n-hexane containing 20% isopropyl alcohol, 1.0 ml/min) to obtain the above-titled compound [I(c-(−))-7] (33.1. mg) in the second peak.

Melting point=164° to 164.5° C. Optical rotation (c=0.5; methyl alcohol)=−76.2° Chemical purity=99.9%

Example 9

[1] Preparation of (2,2-dimethyl)-5R-(4-chlorophenyl)-1R-(1H-1,2,4-triazole-1-ylmethyl)cyclohexane-1-ol [I(c=(+))-8]

The racemic mixture obtained from the Example 8[2] was separated using chiracell OD under the conditions same as those in the Example 8[2] to obtain the above-titled compound [I(c-(+))-8] (31.4 mg) in the first peak.

Melting point=163° to 164° C. Optical rotation (c=0.5; methyl alcohol)=+73.2° Chemical purity=99.9%

The following pharmacological tests were performed using the compounds of the present invention prepared in the Examples 1 to 9. Hereinafter, the compounds of the present invention prepared in the Examples 1 to 9 will be abbreviated as shown in the following Table 1:

TABLE 1

| Compounds of present invention | Abbreviation |
|---|---|
| I(t-(+))-1 | Compound 1 |
| I(t-(−))-2 | Compound 2 |
| I(c-(−))-3 | Compound 3 |
| I(c-(+))-4 | Compound 4 |
| I(t-(+))-5 | Compound 5 |
| I(t-(−))-6 | Compound 6 |
| I(c-(−))-7 | Compound 7 |
| I(c-(+))-8 | Compound 8 |

Example 10

Acute Toxicity

The acute toxicity by forced oral administration was investigated using ICR-JCL mice [male (M) and female (F)]. The compounds 1 to 8 according to the present invention were dissolved or dispersed in polyethyleneglycol 200 or a physiological saline solution. After adjusted to predetermined dose, the solutions or dispersions were administered by a syringe or stomach sonde. After administration, the symptoms of poisoning were continuously observed. The $LD_{50}$ value was determined from the rate of deaths up to the seventh day. The results are shown in Table 2. As the comparative compound, Fluconazol (trade name; hereinafter referred to as FCZ) was used.

TABLE 2

| Tested compounds | $LD_{50}$ value (mg/kg) |
|---|---|
| Compound 1 | >500 (M, F) |
| Compound 2 | >500 (M, F) |
| Compound 3 | >500 (M, F) |
| Compound 4 | >500 (M, F) |
| Compound 5 | >500 (M, F) |
| Compound 6 | >500 (M, F) |
| Compound 7 | >500 (M, F) |
| Compound 8 | >500 (M, F) |
| FCZ | 1388, 1271 (M, F) |

Example 11

Aromatase Activity

The aromarase activity was measured based on the method of Covey et al. [Covey, D. F. et al., BBRC, 157, (1), 81 to 86, 1988]. The aromarase inhibitory activity was determined from the 50% inhibitory concentration ($IC_{50}$ value) of the enzyme activity.

That is, human placental microsome was used as the aromarase enzyme source and [19-$^{14}$C]4-androstene-3,17-dione was used as the substrate. The radioactivity of the $H^{14}COOH$ released in the reaction solution as a result of aromatization was measured to find the enzyme activity radiometrically. Then, a graph of the concentrations of the tested compounds versus the inhibition of the enzyme activity was prepared and the $IC_{50}$ values were found on the graph.

More particularly, a reaction was carried out for 30 minutes in a reaction solution of 0.5 ml of 67 mM phosphate buffer (pH 7.2) while shaking at 37° C., in a system comprised of [19-$^{14}$C]4-androstene-3,17-dione ($1\times10^{-6}$M, 2 kBq/ml), human placenta microsome (0.1 mg/ml protein concentration), coenzyme NADPH ($2\times10^{-3}$M), glucose-6-phosphate ($4\times10^{-3}$M), and glucose-6-phosphate dehydrogenase (4 U/ml). The compounds to be tested were added as a solution in dimethyl sulfoxide (final concentration of dimethyl sulfoxide=0.1 to 0.55%). The $H^{14}COOH$ released in the reaction solution was recovered in the aqueous phase by adding 5 ml of chloroform to the reaction solution at the time of the cessation of the reaction and stirring. 0.1 ml of the aqueous phase was taken and mixed with 4 ml of liquid scintillation cocktail [Atomlight (Dupont)] to measure the radioactivity. The results are shown in Table 3. For comparison, the comparative compound (FCZ) same as in Example 10 was used.

TABLE 3

| Tested compounds | $ID_{50}$ value (µmol/l) |
| --- | --- |
| Compound 1 | $>10^{-6}$ |
| Compound 2 | $>10^{-6}$ |
| Compound 3 | $>10^{-6}$ |
| Compound 4 | $>10^{-6}$ |
| Compound 5 | $>10^{-6}$ |
| Compound 6 | $>10^{-6}$ |
| Compound 7 | $>10^{-6}$ |
| Compound 8 | $>10^{-6}$ |
| FCZ | $>10^{-5}$ |

Example 12

Minimum Inhibitory Concentration

The minimum inhibitory concentrations (MIC) in vitro of the compounds 1 to 8 of the present invention against microorganisms belonging to the genera Candida, Cryptococcus, Aspergillus, and Tricophyton were determined. As a comparative compound, FCZ was used.

(1) The strains of the microorganisms used were as follows. The inoculation solutions were prepared at a concentration of $1\times10^6$ cells/ml.

1) Candida albicans IFO 1060
2) Candida albicans IFO 1270
3) Candida albicans ATCC 762
4) Candida tropicaris IFO 1400
5) Candida krusei IFO 1395
6) Candida parapsilosis IFO 1396
7) Aspergillus fumigatus IFO 5844
8) Aspergillus fumigatus IFO 9733
9) Cryptococcus neoformans 356
10) Tricophyton mentagrophytes TIMM 1189
11) Tricophyton mentagrophytes IFO 5812
12) Tricophyton rubrum TIMM 1216
13) Tricophyton rubrum IFO 9185

(2) As the medium, a Sabouraud dextrose agar medium (Difco: dextrose 2%, agar 1.8%, not adjusted in pH) was used. The samples of the compounds to be tested were used after dissolved in dimethyl sulfoxide. The concentrations of the samples were from 0.1 to 50 µ/ml in the case of the activity of the strains belonging to the genus Tricophyton, and were from 6.25 to 400/ml in the case of the activity of the strains belonging to the genera Candida, Cryptococcus, and Aspergillus.

(3) Procedure

The agar media containing the different concentrations of the compounds to be tested were inoculated with the microorganisms, using a microplanter (Sakuma Seisakusho). The microorganisms belonging to the genera Candida and Cryptococcus were cultured at 27° C. for 3 days, the microorganisms belonging to the genus Aspergillus at 27° C. for 5 days, and the microorganisms belonging to the genus Tricophyton at 27° C. for 7 days. The minimum concentration on the agar medium exhibiting inhibition of growth was used as the minimum inhibitory concentration (MIC). The results are shown in Table 4.

TABLE 4

MIC of Present Compounds Against Various Fungi (µg/ml)

| Compound | Fungi | | | | | | | | | | | | |
| --- | --- | --- | --- | --- | --- | --- | --- | --- | --- | --- | --- | --- | --- |
| | 1 | 2 | 3 | 4 | 5 | 6 | 7 | 8 | 9 | 10 | 11 | 12 | 13 |
| 1 | 50 | 50 | 25 | 100 | 400 | 200 | 200 | 400< | 50 | 50 | 50 | 50 | 50 |
| 2 | 50 | 50 | 50 | 100 | 100 | 6.25 | 100 | 400< | 25 | 25 | 25 | 25 | 25 |
| Racemic mixture of 1 and 2 | 50 | 25 | 50 | 100 | 200 | 25 | 100 | 400< | 50 | 50 | 50 | 50 | 50 |
| 3 | 50 | 100 | 50 | 200< | 200< | 200< | 200< | 400< | 50 | 50< | 50< | 50 | 50 |
| 4 | 50 | 100 | 50 | 200< | 200< | 200< | 200 | 400 | 50 | 50< | 50< | 50 | 50 |
| Racemic mixture of 3 and 4 | 50 | 100 | 50 | 200< | 200< | 200< | 200< | 400< | 100 | 50< | 50< | 50 | 50 |
| 5 | 25 | 25 | 25 | 100 | 200 | 25 | 12.5 | 12.5 | 25 | 50 | 50 | 50 | 50 |
| 6 | 25 | 25 | 12.5 | 100 | 100 | 12.5 | 6.25 | 6.25 | 12.5 | 25 | 50 | 25 | 25 |
| Racemic mixture of 5 and 6 | 25 | 25 | 25 | 100 | 200 | 25 | 12.5 | 12.5 | 12.5 | 50 | 50 | 50 | 50 |
| 7 | 25 | 12.5 | 25 | 50< | 50< | 25 | 50 | 50 | 25 | 50 | 25 | 50 | 50 |
| 8 | 25 | 12.5 | 12.5 | 50< | 50< | 50 | 50 | 50 | 25 | 50< | 50< | 50< | 50< |
| Racemic mixture of 7 and 8 | 25 | 12.5 | 25 | 50< | 50< | 50 | 50 | 50 | 25 | 50< | 50< | 50< | 50< |

TABLE 4-continued

| | MIC of Present Compounds Against Various Fungi (μg/ml) | | | | | | | | | | | | |
|---|---|---|---|---|---|---|---|---|---|---|---|---|---|
| | Fungi | | | | | | | | | | | | |
| Compound | 1 | 2 | 3 | 4 | 5 | 6 | 7 | 8 | 9 | 10 | 11 | 12 | 13 |
| FCZ | 400< | 400< | 400< | 400< | 200 | 12.5 | 400< | 400< | 25 | 400< | 400< | 400< | 400< |

Example 13

Preparation of Capsules

The compound 1 (100 mg) of the present invention, 50 mg of polyoxyethylene sorbitamine monooleate, and 250 mg of starch were thoroughly mixed and filled in capsules to prepare capsules.

INDUSTRIAL APPLICABILITY

The novel azole derivative according to the present invention is low in toxicity, has an antifungal activity, and has an aromarase inhibitory activity (therefore, an antitumor activity). Further, such activities are remarkable when continuously administered.

We claim:

1. A method of inhibiting aromatase, comprising administering to a mammal in need thereof a pharmaceutical composition comprising an effective aromatase inhibiting amount of a compound of formula (I):

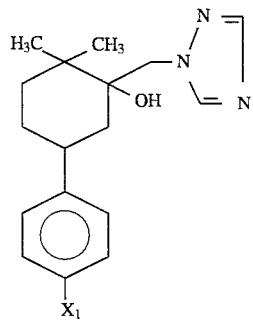

(I)

wherein $X_1$ is a chlorine or fluorine atom, or a pharmaceutically acceptable salt thereof, and a pharmaceutically acceptable carrier.

2. A method according to claim 1, wherein a racemic mixture of compounds of the formulas [I(t-(+))] and [I(t-(−))] are administered:

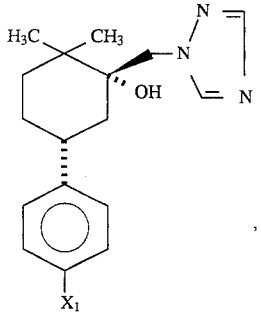

[I(t-(+))]

and

[I(t-(−))]

wherein $X_1$ is a chlorine or fluorine atom, or a pharmaceutically acceptable salt thereof, and a pharmaceutically acceptable carrier.

3. A method according to claim 1, wherein a compound of the formula [I(t-(+))] is administered:

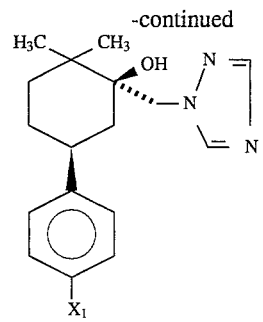

[I(t-(+))]

wherein $X_1$ is a chlorine or fluorine atom, or a pharmaceutically acceptable salt thereof, and a pharmaceutically acceptable carrier.

4. A method according to claim 1, wherein a compound of the formula [I(t-(−))] is administered:

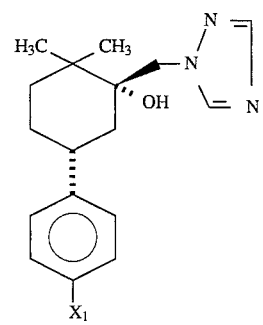

[I(t-(−))]

wherein $X_1$ is a chlorine or fluorine atom, or a pharmaceutically acceptable salt thereof, and a pharmaceutically acceptable carrier.

5. A method according to claim 1, wherein a racemic mixture of compounds of the formulas [I(c-(+))] and [I(c-(−))] are administered:

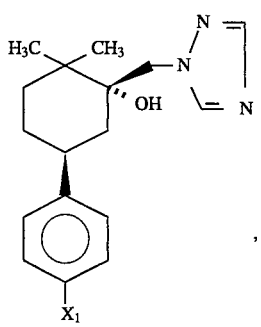
[I(c-(+))]

and

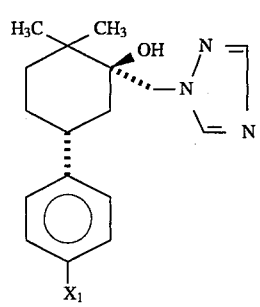
[I(c-(-))]

wherein $X_1$ is a chlorine or fluorine atom, or a pharmaceutically acceptable salt thereof, and a pharmaceutically acceptable carrier.

6. A method according to claim 1, wherein a compound of the formula [I(c-(+))] is administered:

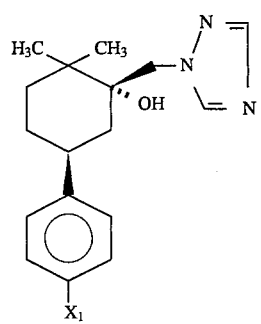
[I(c-(+))]

wherein $X_1$ is a chlorine or fluorine atom, or a pharmaceutically acceptable salt thereof, and a pharmaceutically acceptable carrier.

7. A method according to claim 1, wherein a compound of the formula [I(c-(-))] is administered:

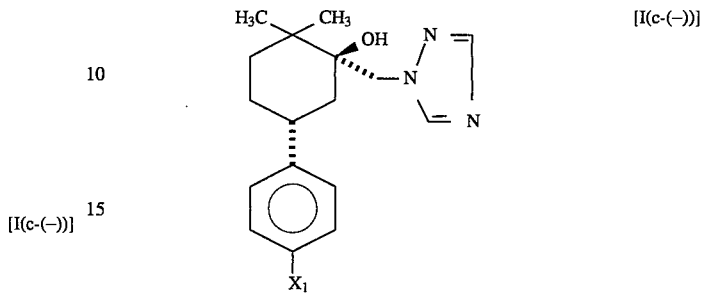
[I(c-(-))]

wherein $X_1$ is a chlorine or fluorine atom, or a pharmaceutically acceptable salt thereof, and a pharmaceutically acceptable carrier.

8. A method according to claim 1, wherein a tumor in the mammal is treated.

9. A method according to claim 2, wherein a tumor in the mammal is treated.

10. A method according to claim 3, wherein a tumor in the mammal is treated.

11. A method according to claim 4, wherein a tumor in the mammal is treated.

12. A method according to claim 5, wherein a tumor in the mammal is treated.

13. A method according to claim 6, wherein a tumor in the mammal is treated.

14. A method according to claim 7, wherein a tumor in the mammal is treated.

* * * * *

UNITED STATES PATENT AND TRADEMARK OFFICE
CERTIFICATE OF CORRECTION

PATENT NO. : 5,508,298
DATED : April 16, 1996
INVENTOR(S) : Koichi NIIMURA et al.

It is certified that error appears in the above-indentified patent and that said Letters Patent is hereby corrected as shown below:

On the title page item [30], line 2, change "Feb. 12, 1992" to --Feb. 15, 1992--

Change "ergos-" to --ergo--- in Column 1, line 33;
Change "terol" to --sterol-- in Column 1, line 34;
Delete "." in Column 1, line 40;
Change "chromatog" to --chromato--- in Column 4, line 12; and
Change "raphy" to -graphy-- in Column 4, line 13

Signed and Sealed this

Fourth Day of March, 1997

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,508,298
DATED : April 16, 1996
INVENTOR(S) : Koichi Niimura, Takao Ando, Toyohiko Nitta, Yuko Ikeda It is certified that error appears in the above-indentified patent and that said Letters Patent is hereby corrected as shown below:

Column 1,     line 29,    delete "3-187464" and insert therefor --3-197464--.

Column 16,    line 26,    delete "$\mu$/ml" and insert therefor --$\mu$g/ml--;

line 28,    delete "400/ml" and insert therefor --400 $\mu$g/ml--.

Signed and Sealed this

Eighteenth Day of November 1997

Attest:

BRUCE LEHMAN

*Attesting Officer*     *Commissioner of Patents and Trademarks*